(12) United States Patent
Schmidt (10) Patent No.: US 7,209,784 B2
(45) Date of Patent: Apr. 24, 2007

(54) HIGH POWER IMPLANTABLE BATTERY WITH IMPROVED SAFETY AND METHOD OF MANUFACTURE

(75) Inventor: Craig L. Schmidt, Eagan, MN (US)

(73) Assignee: Medtronic, Inc., Minneapolis, MN (US)

( * ) Notice: Subject to any disclaimer, the term of this patent is extended or adjusted under 35 U.S.C. 154(b) by 553 days.

(21) Appl. No.: 10/403,114

(22) Filed: Mar. 31, 2003

(65) Prior Publication Data

US 2004/0193227 A1    Sep. 30, 2004

(51) Int. Cl.
*A61N 1/00* (2006.01)
(52) U.S. Cl. .......................................... 607/5
(58) Field of Classification Search .................. 607/5, 607/18; 429/9
See application file for complete search history.

(56) References Cited

U.S. PATENT DOCUMENTS

| | | | |
|---|---|---|---|
| 3,770,504 A | 11/1973 | Bergum | |
| 4,119,720 A | 10/1978 | Hardtmann | |
| 4,204,036 A | 5/1980 | Cohen et al. | |
| 4,375,817 A | 3/1983 | Engle et al. | |
| 4,964,877 A | 10/1990 | Keister et al. | |
| 5,147,737 A | 9/1992 | Post et al. | |
| 5,221,453 A | 6/1993 | Crespi | |
| 5,235,979 A | 8/1993 | Adams | |
| 5,250,373 A | 10/1993 | Muffoletto et al. | |
| 5,306,581 A | 4/1994 | Taylor et al. | |
| 5,312,458 A | 5/1994 | Muffoletto et al. | |
| 5,372,605 A | 12/1994 | Adams et al. | |
| 5,383,907 A | 1/1995 | Kroll | |
| 5,434,017 A | 7/1995 | Berkowitz et al. | |
| 5,439,760 A | 8/1995 | Howard et al. | |
| 5,458,977 A | 10/1995 | Hosokawa et al. | |
| 5,549,717 A | 8/1996 | Takeuchi et al. | |
| 5,674,248 A | 10/1997 | Kroll et al. | |
| 5,814,075 A | 9/1998 | Kroll | 607/5 |
| 5,836,973 A | 11/1998 | Kroll | 607/5 |
| 6,008,625 A | 12/1999 | Gan et al. | |
| 6,038,473 A | 3/2000 | Olson et al. | |

(Continued)

FOREIGN PATENT DOCUMENTS

EP    0 780 918 A1    9/1996

(Continued)

*Primary Examiner*—George Manuel
(74) *Attorney, Agent, or Firm*—Paul H. McDowall; Girma Wolde-Michael (57) ABSTRACT

Implantable medical devices in embodiments of the invention may include one or more of the following features: (a) a hermetic enclosure, (b) a low-power control circuit located in the enclosure, (c) a high-power output circuit located in the enclosure for delivering an electrical pulse therapy, (d) a power source and circuitry located in the enclosure for powering the low-power control circuit and the high-power output circuit, the power source and circuitry, (e) a first high-rate cell, (f) a second high-rate cell electrically connected in parallel to the low-power control circuit and the high-power output circuit, (g) and at least one resistive load electrically connected between the first high-rate cell and the second high-rate cell, the at least one resistive load having a resistive value to limit, in the event of an internal short in one of the high-rate cells, the rate by which the shorted high-rate cell drains the other high-rate cell.

33 Claims, 9 Drawing Sheets

U.S. PATENT DOCUMENTS

| | | |
|---|---|---|
| 6,040,082 A | 3/2000 | Haas et al. |
| 6,044,295 A | 3/2000 | Pilz et al. ............. 607/4 |
| 6,087,809 A | 7/2000 | Gan et al. |
| 6,163,723 A * | 12/2000 | Roberts et al. ......... 607/18 |
| 6,238,813 B1 * | 5/2001 | Maile et al. ............. 429/9 |
| 6,269,266 B1 | 7/2001 | Leysieffer |
| 2001/0033953 A1 | 10/2001 | Gan et al. |
| 2002/0183800 A1 | 12/2002 | Schmidt et al. |
| 2002/0183801 A1 | 12/2002 | Howard et al. ......... 607/34 |

FOREIGN PATENT DOCUMENTS

| | | |
|---|---|---|
| WO | WO 94/02202 A1 | 2/1994 |
| WO | WO 94/22022 A2 | 8/1994 |
| WO | WO 94/22022 A3 | 8/1994 |

* cited by examiner

HIGH POWER IMPLANTABLE BATTERY WITH IMPROVED SAFETY AND METHOD OF MANUFACTURE

FIELD OF THE INVENTION

The present invention relates generally to a power source for an implantable medical device, and more particularly, the present invention relates to a dual cell power source for optimizing implantable medical device performance.

BACKGROUND OF THE INVENTION

A variety of different implantable medical devices (IMD) are available for therapeutic stimulation of the heart and are well known in the art. For example, implantable cardioverter-defibrillators (ICDs) are used to treat those patients suffering from ventricular fibrillation, a chaotic heart rhythm that can quickly result in death if not corrected. In operation, the ICD continuously monitors the electrical activity of a patient's heart, detects ventricular fibrillation, and in response to that detection, delivers appropriate shocks to restore normal heart rhythm. Similarly, an automatic implantable defibrillator (AID) is available for therapeutic stimulation of the heart. In operation, an AID device detects ventricular fibrillation and delivers a non-synchronous high-voltage pulse to the heart through widely spaced electrodes located outside of the heart, thus mimicking transthoratic defibrillation. Yet another example of a prior art cardioverter includes the pacemaker/cardioverter/defibrillator (PCD) disclosed, for example, in U.S. Pat. No. 4,375,817 to Engle, et al. This device detects the onset of tachyarrhythmia and includes means to monitor or detect progression of the tachyarrhythmia so that progressively greater energy levels may be applied to the heart to interrupt a ventricular tachycardia or fibrillation. Numerous other, similar implantable medical devices, for example a programmable pacemaker, are further available.

Regardless of the exact construction and use, each of the above-described IMDs generally includes three primary components: a low-power control circuit, a high-power output circuit, and a power source. The control circuit monitors and determines various operating characteristics, such as, for example, rate, synchronization, pulse width and output voltage of heart stimulating pulses, as well as diagnostic functions such as monitoring the heart. Conversely, the high-power output circuit generates electrical stimulating pulses to be applied to the heart via one or more leads in response to signals from the control circuit.

The power source provides power to both the low-power control circuit and the high-power output circuit. As a point of reference, the power source is typically required to provide 10–20 microamps to the control circuit and a higher current to the output circuit. Depending upon the particular IMD application, the high-power output circuit may require a stimulation energy of as little as 0.1 Joules for pacemakers to as much as 40 Joules for implantable defibrillators.

Suitable power sources or batteries for IMD's are virtually always electrochemical in nature, commonly referred to as electrochemical cells. Acceptable electrochemical cells for IMDs typically include a case surrounding an anode, a separator, a cathode, and an electrolyte. The anode material is typically a lithium metal or, for rechargeable cells, a lithium ion containing body. Lithium batteries are generally regarded as acceptable power sources due in part to their high energy density and low self-discharge characteristics relative to other types of batteries. The cathode material is typically metal-based, such as silver vanadium oxide (SVO), manganese dioxide, etc.

IMDs have several unique power source requirements. IMDs demand a power source with most of the following general characteristics: very high reliability, highest possible energy density (i.e., small size), extremely low self-discharge rating (i.e., long shelf life), very high current capability, high operating voltage, and be hermetic (i.e., no gas or liquid venting).

These unique power source requirements pose varying battery design problems. For example, for the heart monitoring function of an AID, it is desirable to use the lowest possible voltage at which the circuits can operate reliably in order to conserve energy. This is typically in the order of 1.5–3.0 V. On the other hand, the output circuit works most efficiently with the highest possible battery voltage in order to produce firing voltages of up to about 750 V. Traditionally, all manufactured implantable cardioverter defibrillators used a battery system comprised of two cells in series to power the implantable device. This power source of approximately 6 volts provided improved energy efficiency of the output circuit at the expense of energy efficiency of the monitoring circuit. However, a two-cell battery was undesirable from a packaging, cost, and volumetric efficiency perspective.

Eventually, improvements in output circuit design allowed the use of a single 3-volt cell while still maintaining good energy efficiency. Most ICDs are now designed with a single cell battery instead of dual cells connected in series. This approach was taken to improve the volumetric efficiency. In order to achieve the same power capability of the dual cell approach, the electrode surface area of the single cell must be at least equivalent to the total electrode surface area of the dual cell battery. However, the increased electrode surface area of a single cell poses a potential hazard to the IMD should an internal short circuit develop in the battery cell. If the electrode surface area is too high (approximately above 90 $cm^2$ for a Li/SVO battery) and an internal short develops, the battery can get hot enough to potentially destroy the IMDs electronics and possibly burn the patient. As a result, most IMD and IMD battery manufacturers have adopted a design rule, which limits the surface area of a single cell to approximately 90 $cm^2$. This is significantly less surface area than a typical dual cell design where the surface area was approximately 130 $cm^2$. Hence, these single cell ICD batteries produced less power and the result was longer capacitor charge times. Many studies have proposed that defibrillation and cardioversion shocks are most effective when delivered as quickly as possible following detection of arrhythmia. The chance of terminating an arrhythmia in a patient decreases as the length of time it takes for therapy to be delivered to the patient increases. Therefore, the shorter the charge time for the capacitors the more effective the defibrillation therapy. Typically, battery electrode sizes are inversely proportional to the charging time. Therefore, the quicker the desired charging time, the larger the battery.

While single battery systems have proved workable for implantable cardioverter defibrillators, the use of a single battery system necessarily involves a compromise between the ideal power supply and the hazards associated with large surface area electrodes. Accordingly, it would be desirable to provide for an improved dual battery power system for an implantable cardioverter defibrillator, which overcomes the problems of earlier attempts at dual battery systems.

BRIEF SUMMARY OF THE INVENTION

Implantable medical devices in embodiments of the invention may include one or more of the following features: (a) a hermetic enclosure, (b) a low-power control circuit located in the enclosure, (c) a high-power output circuit located in the enclosure for delivering an electrical pulse therapy, (d) a power source and circuitry located in the enclosure for powering the low-power control circuit and the high-power output circuit, the power source and circuitry, (e) a first high-rate cell, (f) a second high-rate cell wherein the first cell and second cell are electrically connected in parallel to the low-power control circuit and the high-power output circuit, (g) at least one resistive load electrically connected between the first high-rate cell and the second high-rate cell, the at least one resistive load having a resistive value to prevent, in the event of an internal short in one of the high-rate cells, the shorted high-rate cell from substantially draining the other high-rate cell wherein either high rate cell is able to provide power for both the low-power control circuit and the high-power output circuit, in the event of a short in the other high rate cell, and (h) a switching circuit electrically connected between the first high-rate cell and the second high-rate cell for selectively coupling the first high-rate cell to the second high-rate cell upon activation of the high-power output circuit.

An electrochemical battery of the invention may include one or more of the following features: (a) a first high-rate electrochemical cell comprising: a first anode with a first anode current collector, a first terminal for connecting the first anode current collector to a first external lead, and a first electrolyte operatively associated with the first anode, (b) a second high-rate electrochemical cell comprising: a second anode with a second anode current collector; a second terminal for connecting the second anode current collector to a second external lead; and a second electrolyte operatively associated with the second anode, (c) a cathode electrically associated with the first electrolyte and the second electrolyte, wherein the first cell is connected in parallel to the second cell; and (d) at least one resistive load electrically connected between the first external lead and the second external lead. Of course, the cathode could be the external lead, or both anode and cathode could be connected to external leads.

Methods of manufacturing an electrochemical battery according to the present invention may include one or more of the following steps: (a) providing a first high-rate electrochemical cell, comprising the steps of: providing a first cathode with a first cathode current collector, connecting a first external lead to the first cathode current collector, and activating the first high-rate cell with an electrolyte solution operatively associated with the first cathode, (b) providing a second high-rate electrochemical cell, comprising the step of: providing a second cathode with a second cathode current collector, connecting a second external lead to the second cathode current collector, and activating the second electrochemical cell with the electrolyte solution operatively associated with the second cathode, (c) associating an anode electrically with the electrolyte in the first high-rate cell and the second high-rate cell, wherein the first cell is connected in parallel to the second cell, (d) connecting at least one resistive load electrically between the first external lead and the second external lead and (e) connecting the anode to a battery casing to provide a negative charge on the casing.

Methods for manufacturing an implantable medical device according to the present invention may include one or more of the following steps: (a) providing a hermetic enclosure, (b) providing a low-power control circuit in the enclosure, (c) providing a high-power output circuit in the enclosure for delivering an electrical pulse therapy, (d) providing a power source and circuitry in the enclosure for powering the low-power control circuit and the high-power output circuit, (e) providing a first high-rate cell, (f) providing a second high-rate cell, (g) connecting the first cell and second cell electrically in parallel to the low-power control circuit and the high-power output circuit, (h) connecting at least one resistive load electrically between the first high-rate cell and the second high-rate cell, and (i) connecting a switching circuit electrically between the first high-rate cell and the second high-rate cell for selectively coupling the first high-rate cell to the second low-rate cell upon activation of the high-power output circuit.

DETAILED DESCRIPTION OF THE PREFERRED EMBODIMENTS

The following detailed description is to be read with reference to the figures, in which like elements in different figures have like reference numerals. The figures, which are not necessarily to scale, depict selected embodiments and are not intended to limit the scope of the invention. Skilled artisans will recognize that the examples provided herein have many useful alternatives that fall within the scope of the invention.

Figure 1:
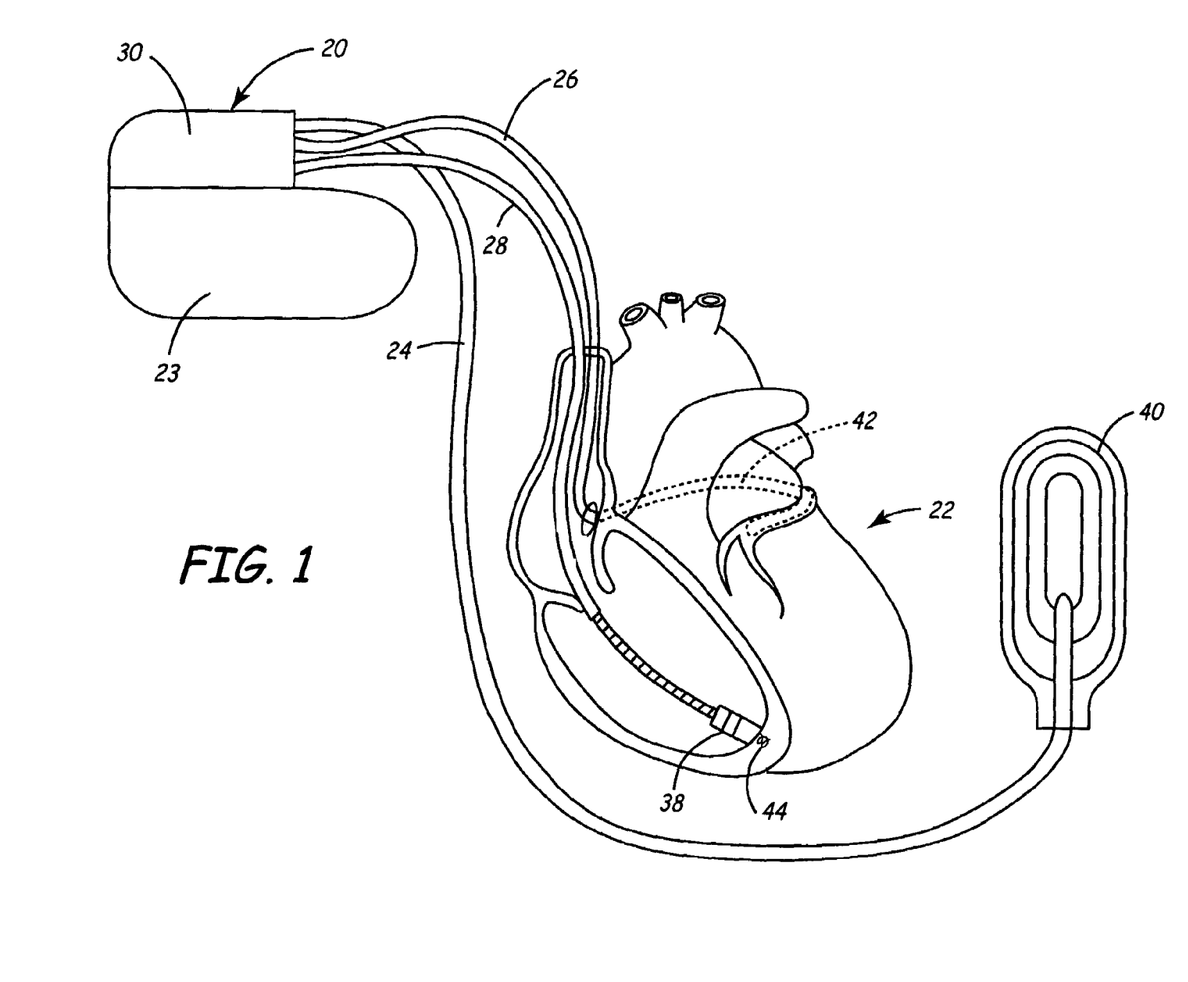
FIG. 1 is a simplified schematic view of one embodiment of an implantable medical device (IMD) incorporating a power source in accordance with the present invention.

FIG. 1 is a simplified schematic view of one embodiment of an implantable medical device ("IMD") 20 in accordance with the present invention and its relationship to a human heart 22. The IMD 20 is shown in FIG. 1 as preferably being a pacemaker/cardioverter/defibrillator (PCD), although the IMD may alternatively be a drug delivery device, a neuro-stimulator, or any other type of implantable device known in the art. The IMD includes a case or hermetic enclosure 23 and associated electrical leads 24, 26, and 28. As described in greater detail below, the enclosure case 23 contains various circuits and a power source. The leads 24, 26 and 28 are coupled to the IMD 20 by means of a multi-port connector block 30, which contains separate ports for each of the three leads 24, 26, and 28 illustrated.

In one embodiment, lead 24 is coupled to a subcutaneous electrode 40, which is intended to be mounted subcutaneously in the region of the left chest. Alternatively, an active "can" may be employed such that stimulation is provided between an implanted electrode and enclosure case 23. In yet another embodiment, stimulation is provided between two electrodes carried on a single multipolar lead.

The lead 26 is a coronary sinus lead employing an elongated coil electrode that is located in the coronary sinus and great vein region of the heart 22. The location of the electrode is illustrated in broken line format at 42, and extends around the heart 22 from a point within the opening of the coronary sinus to a point in the vicinity of the left atrial appendage.

Lead 28 is provided with an elongated electrode coil 38, which is located in the right ventricle of the heart 22. The lead 28 also includes a helical stimulation electrode 44, which takes the form of an extendable/retractable helical coil, which is screwed into the myocardial tissue of the right ventricle. The lead 28 may also include one or more additional electrodes for near and far field electrogram sensing.

In the system illustrated, cardiac pacing pulses are delivered between the helical electrode 44 and the coil electrode 38. The electrodes 38 and 44 are also employed to sense electrical signals indicative of ventricular contractions. Additionally, cardioverters/defibrillation shocks may be delivered between coil electrode 38 and the electrode 40, and between coil electrode 38 and electrode 42. During sequential pulse defibrillation, it is envisioned that pulses would be delivered sequentially between subcutaneous electrode 40 and coil electrode 38, and between the coronary sinus electrode 42 and coil electrode 38. Single pulse, two electrode defibrillation pulse regimens may also be provided, typically between coil electrode 38 and the coronary sinus electrode 42. Alternatively, single pulses may be delivered between electrodes 38 and 40. The particular interconnection of the electrodes to the IMD 20 will depend somewhat on the specific single electrode pair defibrillation pulse regimen is believed more likely to be employed.

Figure 2:
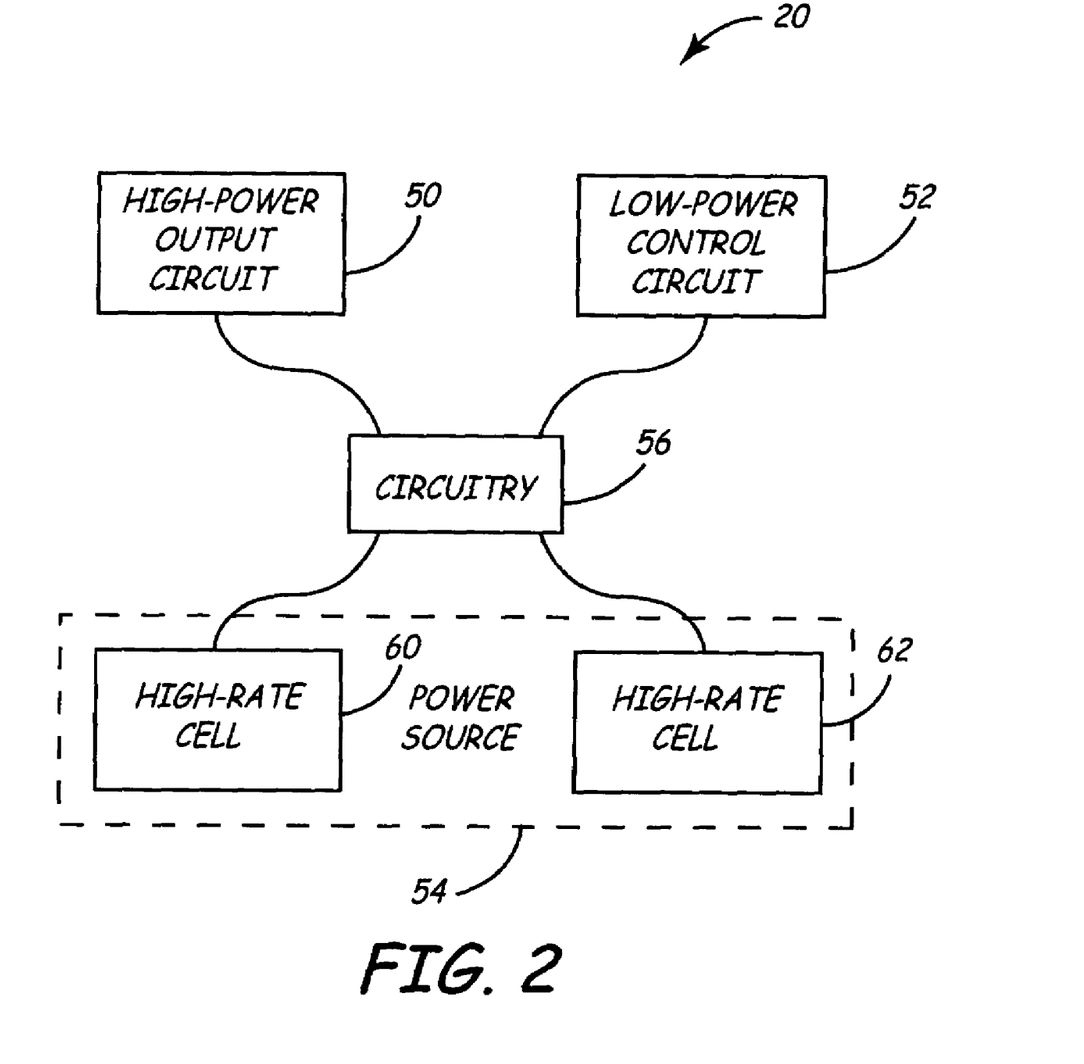
FIG. 2 is a simplified schematic circuit diagram of a power source in accordance with the present invention for use with the IMD of FIG. 1.

Regardless of the exact configuration and operation of the IMD 20, the IMD 20 includes several basic components, illustrated in block form in FIG. 2. The IMD 20 includes a high-power output circuit 50, a low-power control circuit 52, a power source 54 (shown with dashed lines), and circuitry 56. As described in greater detail below, the power source 54 is preferably a dual-cell configuration, and can assume a wide variety of forms. Similarly, the circuitry 56 can include analog and/or digital circuits, can assume a variety of configurations, and electrically connects the power source 54 to the high power circuit 50 and the low-power circuit 52.

The high-power output circuit 50 and the low-power control circuit 52 are typically provided as part of an electronics module associated with the IMD 20. In general terms, the high-power output circuit 50 is configured to deliver an electrical pulse therapy, such as a defibrillation or a cardioversion/defibrillation pulse. In sum, the high-power output circuit 50 is responsible for applying stimulating pulse energy between the various electrodes 38–44 (FIG. 1) of the IMD 20. As is known in the art, the high-power output circuit 50 may be associated with a capacitor bank (not shown) for generating an appropriate output energy, for example in the range of 0.1–40 Joules.

The low-power control circuit 52 is similarly well known in the art. In general terms, the low-power control circuit 52 monitors heart activity and signals activation of the high-power output circuit 50 for delivery of an appropriate stimulation therapy. Further, as known in the art, the low-power control circuit 52 may generate a preferred series of pulses from the high-power output circuit 50 as part of an overall therapy.

The power source 54 and associated circuitry 56 can assume a wide variety of configurations, as described in the various embodiments below. Preferably, however, the power source 54 includes a first, high-rate cell 60, and a second, high-rate cell 62. However, it is fully contemplated that power source 54 could contain a plurality of high-rate cells within volumetric reason so that IMD 20 does not become to large for implantation or uncomfortable to the patient. Notably the first and second cells 60, 62 can be formed separate from one another or contained within a singular enclosure. However, as is discussed below, preferably cells 60, 62 are contained within a singular enclosure. First and second cells can 60, 62 can have any amount of electrode surface area within reason to deliver the proper amount of surface energy. However, preferably cells 60, 62 have an electrode surface area of between 45 $cm^2$ and 90 $cm^2$ each to provide high power output. Depending upon the particular application, high-rate cells 60, 62 are configured to provide a stimulation energy of as little as 0.1 Joules for pacemakers to as much as 40 Joules for implantable defibrillators. As described below with reference to specific embodiments, high-rate cells 60, 62 can assume a wide variety of forms as is known in the art. Preferably, high-rate cells 60, 62 include an anode, a cathode, and an electrolyte. The anode is preferably formed to include lithium, either in metallic form or ion form for re-chargeable applications. With this in mind, high-rate cells 60, 62 are most preferably a spirally wound battery of the type disclosed, for example, in U.S. Pat. No. 5,439,760 to Howard et al. for "High Reliability Electrochemical Cell and Electrode Assembly Therefor" and U.S. Pat. No. 5,434,017 to Berkowitz et al. for "High Reliability Electrochemical Cell and Assembly Therefor," the disclosures of which are hereby incorporated by reference. High-rate cells 60, 62 may less preferably be a battery having a spirally wound, stacked plate, or serpentine electrodes of the type disclosed, for example, in U.S. Pat. Nos. 5,312,458 and 5,250,373 to Muffuletto et al. for "Internal Electrode and Assembly Method for Electrochemical Cells;" U.S. Pat. No. 5,549,717 to Takeuchi et al. for "Method of Making Prismatic Cell;" U.S. Pat. No. 4,964,877 to Kiester et al. for "Non-aqueous Lithium Battery;" and U.S. Pat. No. 5,14,737 to Post et al. for "Electrochemical Cell With Improved Efficiency Serpentine Electrode;" the disclosures of which are herein incorporated by reference.

Materials for the cathode of high-rate cells 60, 62 are most preferably solid and comprise as active components thereof metal oxides such as vanadium oxide, silver vanadium oxide (SVO) or manganese dioxide, as is known in the art. Alternatively, the cathode for high-rate cells 60, 62 may also comprise carbon monofluoride and hybrids thereof or any other active electrolytic components and combination. Where SVO is employed for the cathode, the SVO is most preferably of the type known as "combination silver vanadium oxide" (or "CSVO") as disclosed in U.S. Pat. Nos. 5,221,453; 5,439,760; and 5,306,581 to Crespi et al, although other types of SVO may be employed.

It is to be understood that electrochemical systems other than those set forth explicitly above may also be utilized for high-rate cells 60, 62, including, but not limited to, anode/ cathode systems such as lithium/silver oxide; lithium/manganese oxide; lithium/$V_2O_5$; lithium/copper silver vanadium oxide; lithium/copper oxide; lithium/lead oxide; lithium/carbon monofluoride; lithium/chromium oxide; lithium/bismuth-containing oxide; lithium/copper sulfate; mixtures of various cathode materials listed above such as a mixture of silver vanadium oxide and carbon monofluoride; and lithium ion rechargeable batteries, to name but a few.

Figure 3:
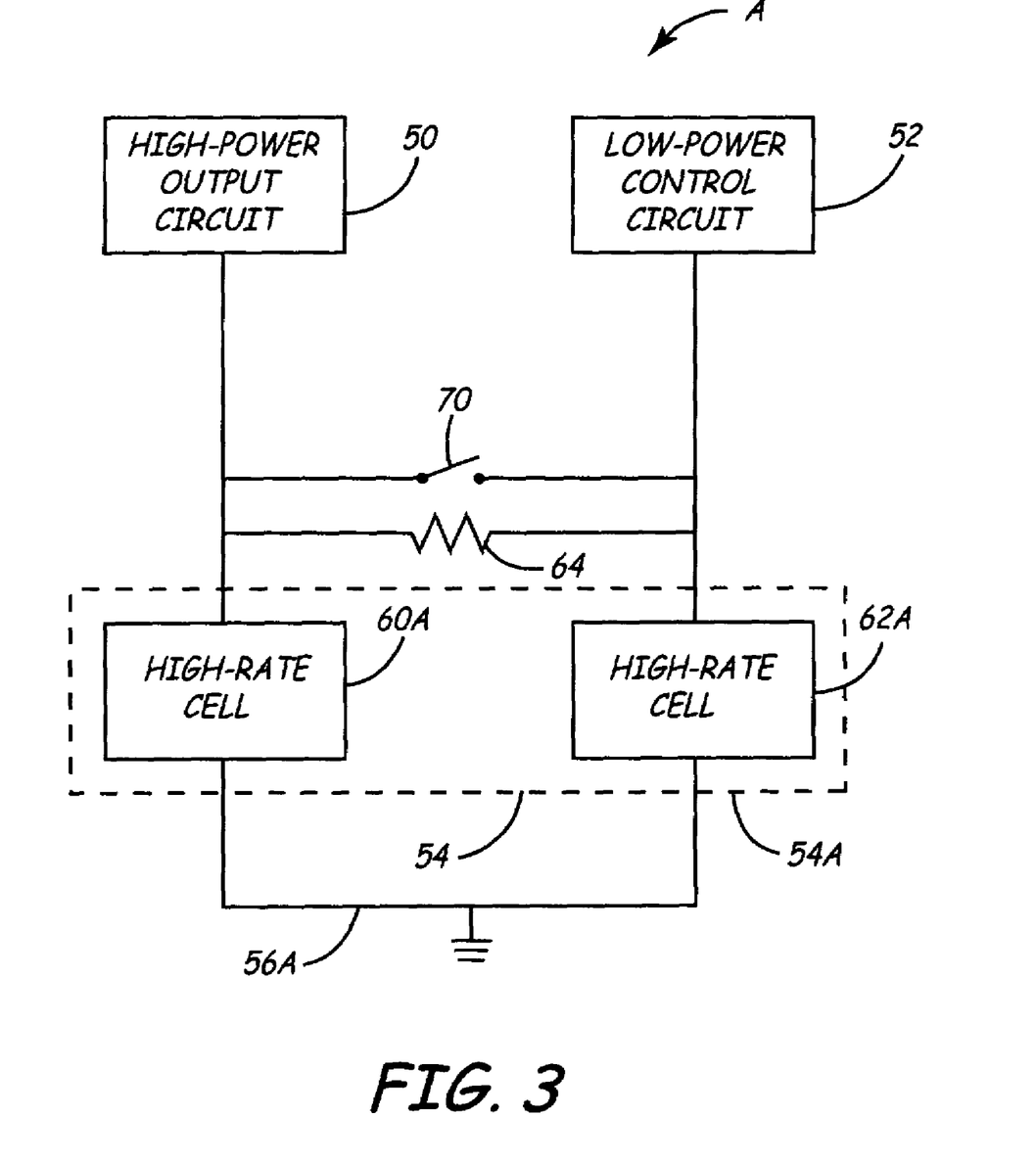
FIG. 3 is a simplified schematic diagram of an embodiment for a power source in accordance with the present invention.

With the above-described parameters of high-rate cell 60 and high-rate cell 62 in mind, one preferred combination of a power source 54A and circuitry 56A is depicted schematically in FIG. 3. The power source 54A includes high-rate cell 60A and high-rate cell 62A as described above. Unlike U.S. pub. No. 2002/0183801 A1 herein incorporated in its entirety by reference, which includes a high-rate and low-rate cell selectively connected in parallel, circuitry 56A electrically connects high-rate cell 60A and high-rate cell 62A in parallel to high-power output circuit 50 and low-power control circuit 52. In particular, the circuitry 56A includes a switch 70 configured to selectively couple high-rate cells 60A and 62A to high-power control circuit 50. In this regard, circuitry 56A can include additional components/connections (not shown) for activating and deactivating switch 70 in response to operational conditions described below. Circuitry 56A further includes resistive load 64 to limit the current delivered from a non-shorted cell to a shorted cell in the event of an internal short within one of cells 60A or 62A.

This battery circuit design allows two high-rate cells to be connected in parallel to achieve the same power capability as two cells connected in series. Resistor 64 is selected such that $R \geq 10R_{Cell}$ where R is the resistance of resistive load 64 and $R_{Cell}$ is the resistance of high-rate cell 60 or 62. However, preferably $R \geq 100R_{Cell}$ and $R << 10R_{Circuit}$ where $R_{Circuit}$ is the input impedance of low-power circuitry 52. Generally, R can be any reasonable value within the specifications above, but preferably R is between 10–100 ohms and $R_{Cell}$ is approximately 0.5 ohm. This resistive relationship allows both cells 60A and 62A to be discharged uniformly under pacing and sensing conditions, which is described in more detail below.

In normal operation, switch 70 is open until it is necessary to deliver a defibrillation pulse and then the switch is closed. Switch 70 is selected such that $R_{Switch} << R << R_{Charge}$, where $R_{Charge}$ is the input impedance of high-power circuitry 50. Switch 70 is closed only when charging a defibrillation capacitor (not shown) and would be enabled only when the voltage across load 64 was below a pre-determined value of approximately 20 millivolts indicating that neither cell 60A nor 62A has an internal short. If switch 70 was enabled when either cell 60A or 62A had an internal short, then the current from the non-shorted cell would dissipate into the shorted battery and would quickly deplete both cells, create enough heat to damage circuitry, and possibly cause discomfort the patient. In an alternative embodiment load 64 could be substituted with a fuse.

This power source/circuitry configuration provides a distinct advantage over prior art, single-cell and dual-cell in series designs. The primary advantage is two high-rate cells can be assembled in parallel in the same enclosure. This is generally 20% more volumetrically efficient than two cells in series. Further, the risk of damage to the IMD and harm to the patient is substantially reduced. Another advantage of the present invention is that it allows single cell electronic circuits to be retrofitted to a parallel two-cell design with significantly minimal circuit design changes. During operation of the IMD 20 (FIG. 1), the power source 54A is, from time-to-time, required to deliver a high-current pulse or charge to high-power output circuit 50 while maintaining a voltage high enough to continuously power low-power control circuit 52. If the supply voltage drops below a certain value, the IMD 20 will cease operation. This power source/circuitry configuration places the high-rate cells 60A and 62A in parallel to power both low-power control circuit 52 and when necessary high-power circuit 50. During a transient high power pulse, such as a defibrillation pulse, the switch 70 is operated to couple high-rate cell 60A with high-rate cell 62A with minimal resistance and therefore substantially all the power from cells 60A and 62A is transferred to high-power circuit 50. The low battery resistance provided by the parallel combination of cells 60A and 62A prevents an excessive voltage drop during a transient high power pulse and assures continuous operation of low-power circuit 50. Further, where desired, the cells 60A and/or 62A can be sized and shaped to satisfy certain volumetric or shape constraints presented by the IMD 20 (FIG. 1).

With reference again to FIG. 3, if an internal short were to occur within either cell 60A or 62A and resistive load 64 were not in circuit 56A, then cell 62A would begin to discharge into cell 60A until cell 62A was depleted beyond usefulness. This would make IMD 20 unable to provide therapeutic stimulation and thus IMD 20 would have to be explanted and another IMD implanted. Further, the short would create a lot of heat, which could destroy the electronics of the IMD and cause potentially serious discomfort to the patient. However, with resistive load 64 between cell 60A and 62A in circuit 56A, cell 62A is limited in the amount of power that can be delivered to shorted cell 60A due to the parallel construction.

The parallel battery construction of the present invention allows cells 60A and 62A to deplete at an equal rate over the life of IMD 20. For example, when a defibrillation pulse is needed, switch 70 is closed, after it is determined that there is no internal short in cells 60A or 62A, and cells 60A and 62A begin discharging into high-power circuit 50. The only difference in the current path between cell 60A and 62A is that the current path for cell 62A must travel through the resistance of switch 70. It's of note that the current path is generally through switch 70 and not resistor 64 since current will take the path of least resistance. Therefore, since $R_{Switch}$ has a lower value than load 64, the current path from cell 62A will be through switch 70. Since switch 70 has a small resistance, cell 60A and 62A will deplete at a substantially equal rate during defibrillation pulses since there is a minimal voltage drop at switch 70.

In a similar fashion, when cells 60A and 62A are powering low-power circuit 52 the only difference in the current path between cell 60A and 62A is that the current path for cell 60A must travel through load 64. Since load 64 has a relatively small resistance and the current traveling through load 64 is between 10–20 microamps, then the voltage drop at load 64 is extremely low, approximately between 0.1 and 2 millivolts, and therefore cell 60A and 62A will deplete at a substantially equal rate while supplying low-power circuit 52.

Figure 4:
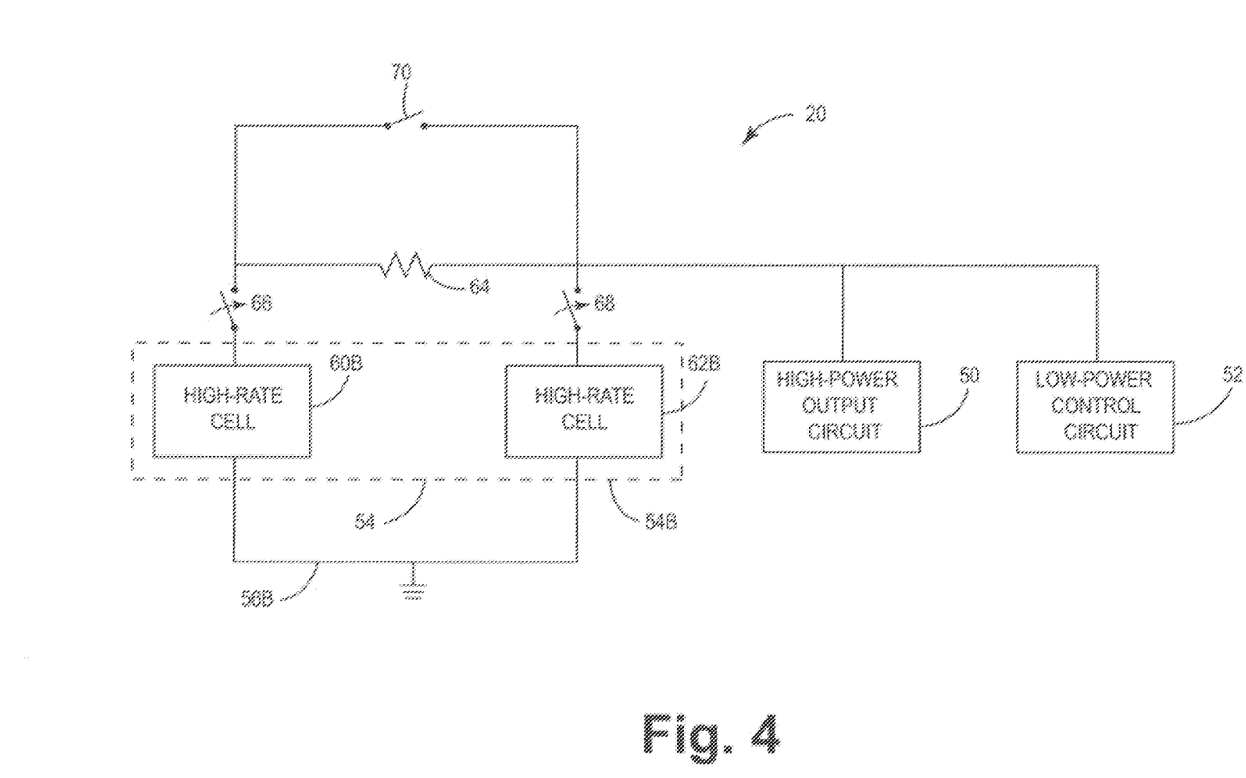
FIG. 4 is a simplified schematic diagram of another embodiment for a power source in accordance with the present invention.

With reference to FIG. 4, another embodiment for a power source is shown. The circuit is substantially the same as the circuit in FIG. 3, except that switches 68 and 66 have been added to circuit 56B. The circuit of FIG. 4 allows for one of cells 60B and 62B to become a backup should the other one experience an internal short. For example, normally switches 68 and 66 are closed to provide normal operation or the circuit and IMD 20. However, should a short be detected on load 64, switch 66 is opened. If current ceases to flow through load 64, then it is determined that an internal short has occurred in high-rate cell 60B and switch 68 is opened and switch 66 is closed again to provide power to IMD 20. If current continues to flow through load 64, then it is determined that an internal short has occurred in high-rate cell 62B and switch 66 remains closed. Since each cell 60B and 62B is a high-rate cell, IMD 20 is able to function normally, except for a slower defibrillation capacitor-charging time, until cell 50B becomes depleted enough and explanting is necessary. One additional embodiment associated with FIG. 4. On rare occasion the failure of a circuit component can effectively short circuits the battery. The heat generated during this failure mode can cause significant discomfort to the patient. With the design shown in FIG. 4, an external short would also show up as a voltage drop across load 64. The same algorithm described forces one cell to effectively disconnect, thereby greatly reducing the rate of energy dissipation due to the short.

Figure 5:
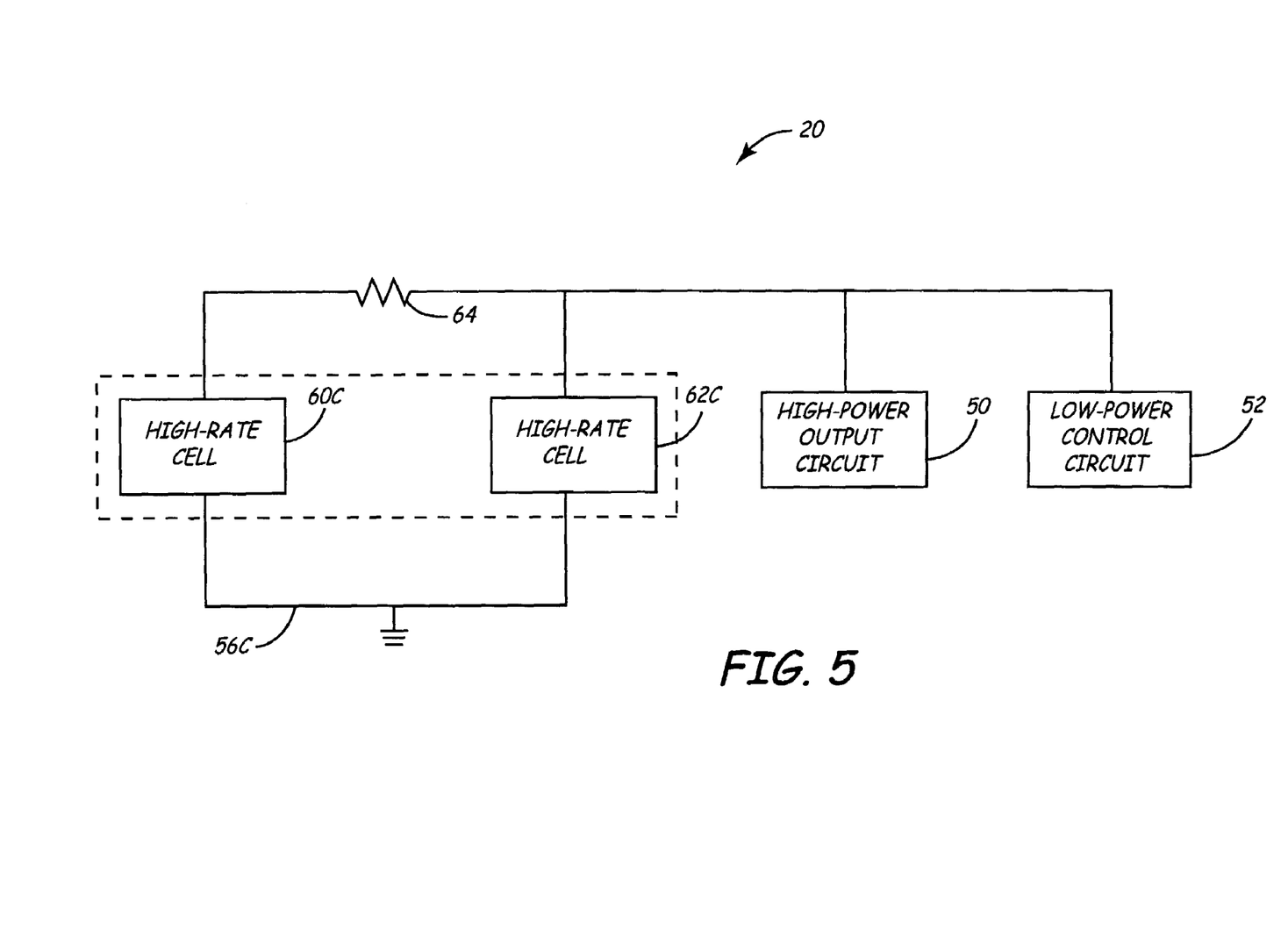
FIG. 5 is a simplified schematic diagram of another embodiment for a power source in accordance with the present invention.

With reference to FIG. 5, another embodiment for a power source is shown. The circuit is similar to the circuit of FIG. 3 except that switch 70 has been removed. This embodiment still protects IMD 20 from an internal short, however, this embodiment is much more inefficient when operating in a defibrillating mode. This is because the current from cell 60C must travel through load 64. This creates a large voltage drop at load 64 and thus it takes longer to fully charge the defibrillation capacitor.

Figure 6:
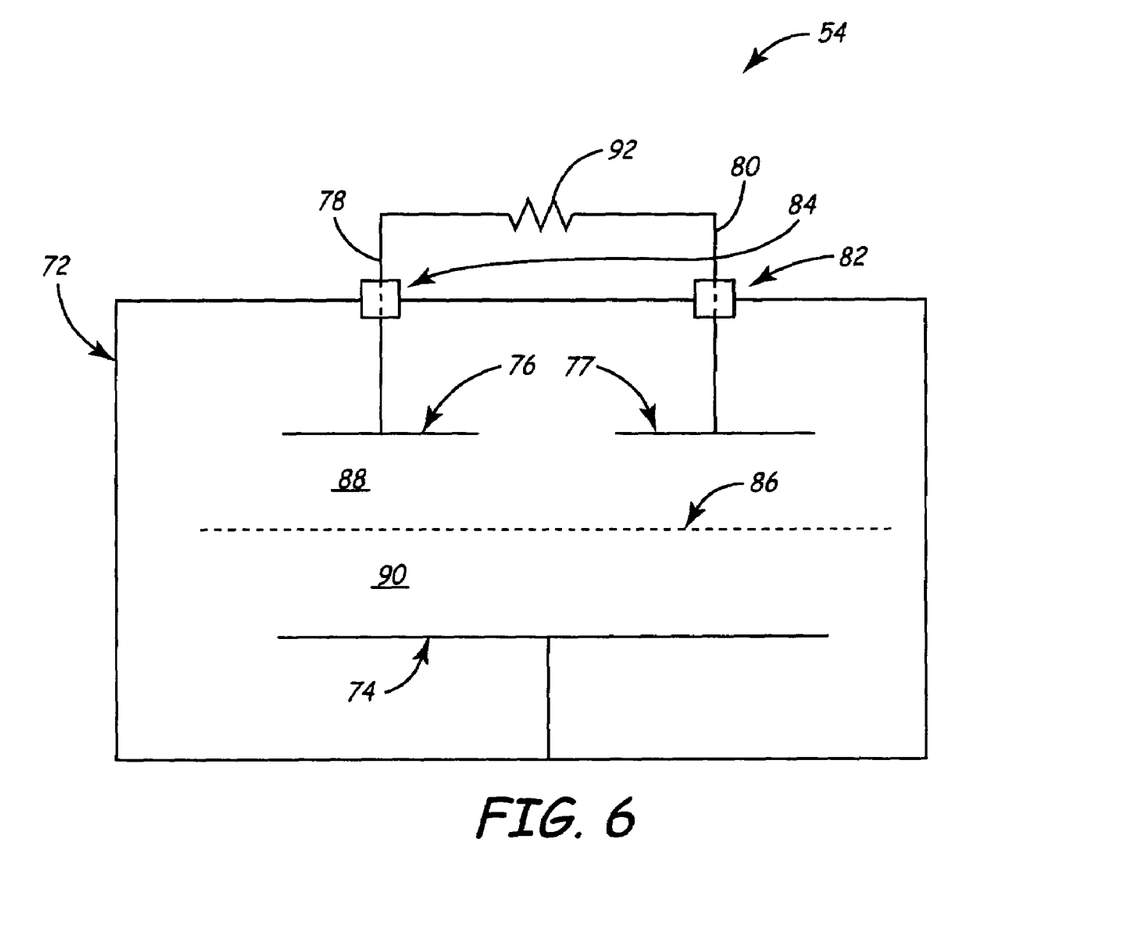
FIG. 6 is a simplified schematic diagram of a high-rate dual-cell battery embodiment in accordance with the present invention.

With reference to FIG. 6, a simplified schematic of a high-rate dual cell battery is shown. In this embodiment power source 54 is shown having battery case 72, anode 74, cathode 76, cathode 77, separator 86, feedthrough 84, feedthrough 82, terminal 78, and terminal 80. Battery case 72 is shown in dotted lines, as the casing can be variable in shape and construction. Battery case 72 can be a deep drawn case as discussed in U.S. Pat. No. 6,040,082 (Haas et. al.) herein incorporated in its entirety by reference or a shallow drawn case as discussed in U.S. patent application Ser. No. 10/260,629 attorney docket number P-10765.00 filed on Sep. 30, 2002 titled Contoured Battery for Implantable Medical Devices and Method of Manufacture herein incorporated in its entirety by reference. Battery case 72 is preferably made of a medical grade titanium, however, it is contemplated that battery case 72 could be made of almost any type of material, such as aluminum and stainless steel, as long as the material is compatible with the battery's chemistry in order to prevent corrosion. Further, it is contemplated that battery case 72 could be manufactured from most any process including but not limited to machining, casting, thermoforming, or injection molding.

In the embodiment of FIG. 6, one electrode 74 is continuous and is connected to case 72. The alternate electrode is in two separate pieces 76 and 77. Each piece 76 and 77 has a separate electrical lead 78 and 80 through a feedthroughs 84 and 82 respectively that is electrically isolated from case 72. It is contempleated that battery 54 can be case negative (anode connected to case) or case positive (cathode connected to case). As shown, dual cell battery 54 has one anode 74, which is utilized by a first cell chamber 88 and a second cell chamber 90, which are separated by separator 86. There is no requirement of a hermetic seal between cells 88 and 90. They could be designed this way, but it would be an unnecessary complication and result in a decrease in volumetric efficiency. Separator 86 is used to prevent direct electrical contact between anode 74 and cathodes 76 and 77. It is a porous material that allows transport of electrolyte ions. Li/SVO batteries typically use separators comprised of porous polypropylene or polyethylene, but there are many other materials used for other battery chemistries. Nevertheless, separator 86 is not required for the present invention and can and power source 54 can operate without it. Further, it is noted that the anode/cathode relationship could be reversed. For example, anode 74 could be replaced with a cathode as long as cathodes 76 and 77 were switched to anodes. It is understood that the orientation of the anodes and cathodes is not a critical aspect of the invention. Although lithium hexafluoroarsenate is preferably used in both cells 88 and 90 for the present embodiment, it is contemplated that most any chemical electrolyte could be used without departing from the spirit of the invention for either cell chamber 88 or 90. Cathodes 76 and 77 are located within cells 88 and 90 respectively and are connected to external leads 78 and 80 respectively, which traverse out of battery case 72 through feedthroughs 84 and 82. While power source 54 is shown with two feedthroughs, it is fully contemplated that battery case 72 could have one feedthrough to accommodate both leads 78 and 80. Finally, resistive load 92 is shown connected between leads 78 and 80. As discussed above, load 92 functions to limit the amount of power delivered from a non-shorted cell to a shorted cell.

Figure 7:
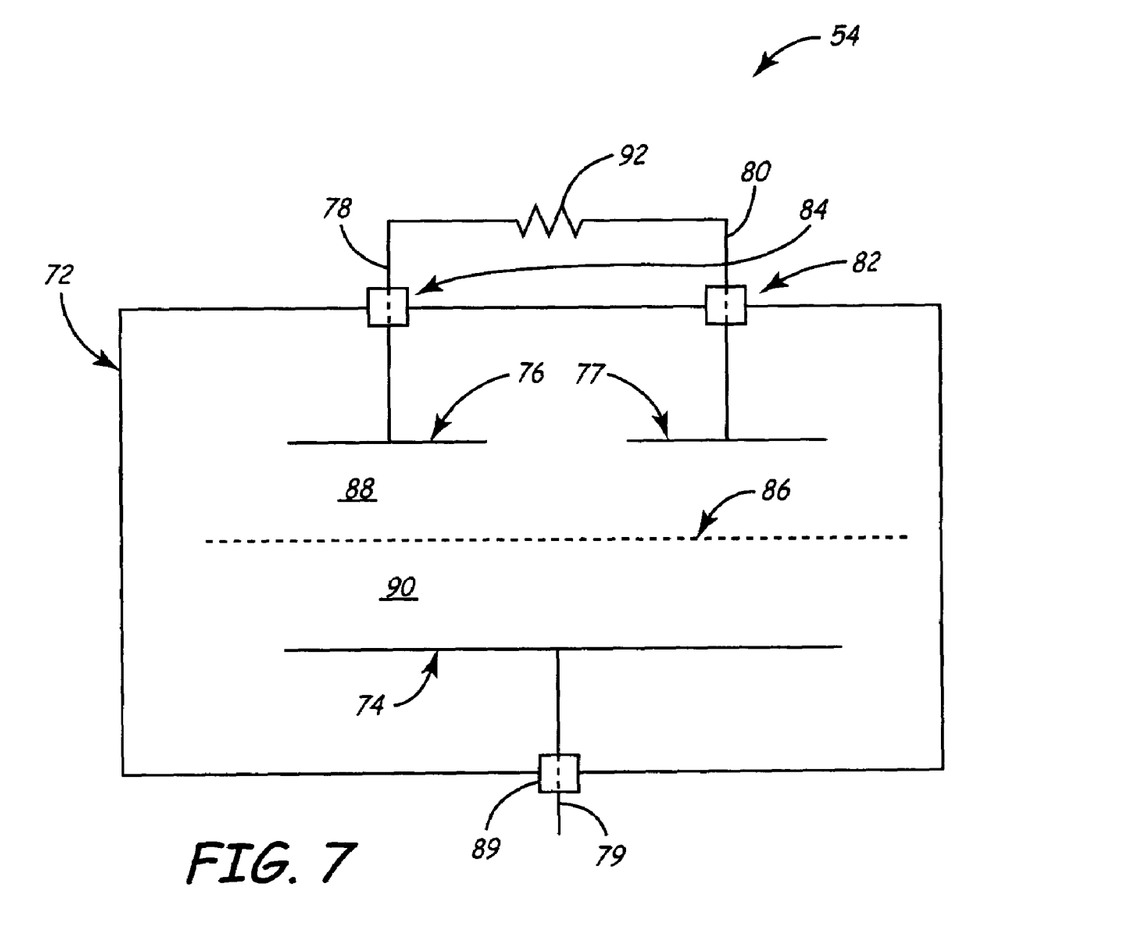
FIG. 7 is a simplified schematic diagram of another high-rate dual-cell battery embodiment in accordance with the present invention.

With reference to FIG. 7, a simplified schematic of another high-rate dual cell battery is shown. In contrast to the dual cell embodiment of FIG. 6, continuous electrode 74 is not connected to case 72. Instead electrical lead 79 extends through feedthrough 89 to make case 72 neutral.

Figure 8:
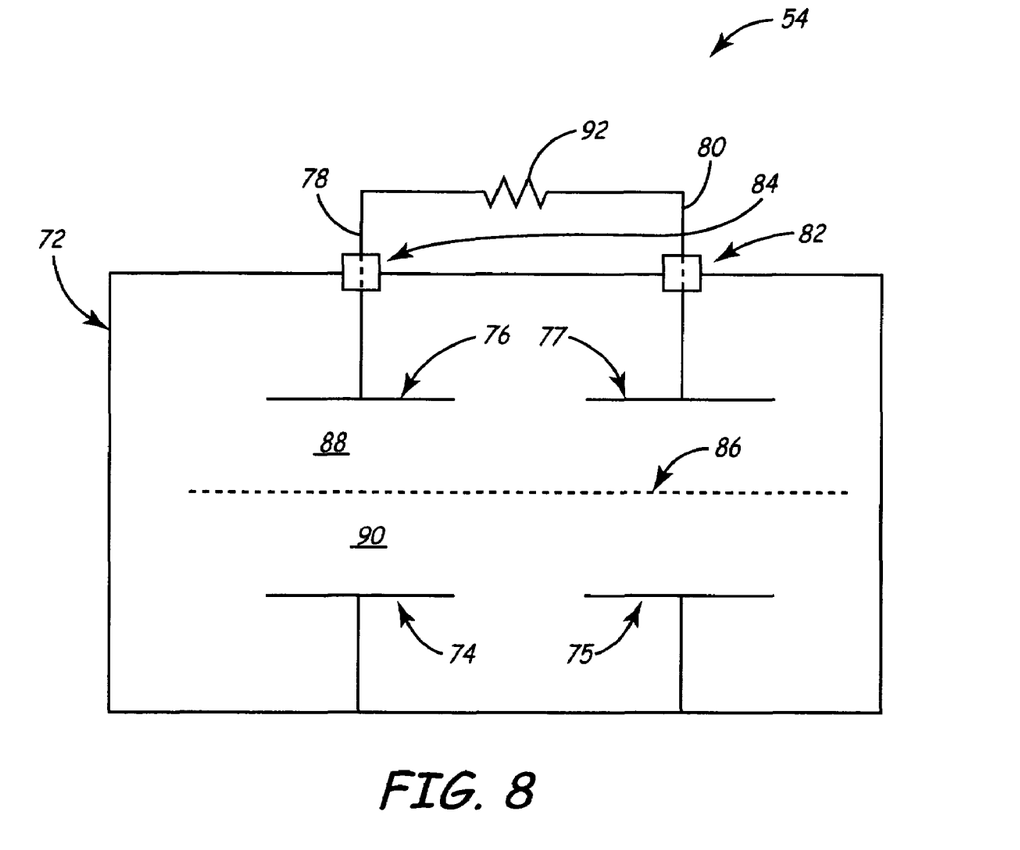
FIG. 8 is a simplified schematic diagram of another high-rate dual-cell battery embodiment in accordance with the present invention.

With reference to FIG. 8, a simplified schematic of another high rate dual battery is shown. In contrast to the dual cell embodiment of FIG. 6, the anode is not continuous and each piece 74 and 75 is connected to case 72. This would be equivalent to taking two completely separate cells and placing them in the same battery case.

Figure 9:
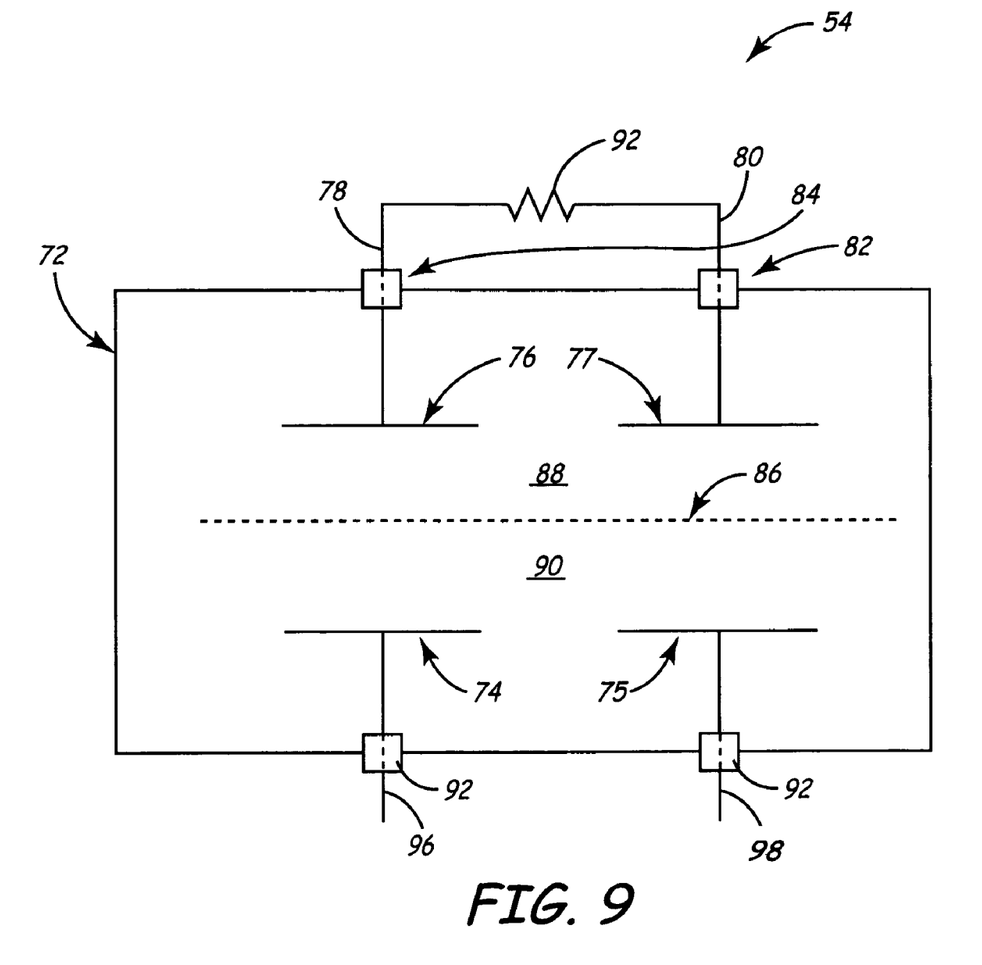
FIG. 9 is a simplified schematic diagram of another high-rate dual-cell battery embodiment in accordance with the present invention.

With reference to FIG. 9, a simplified schematic of another high rate dual battery is shown. This design is similar to the embodiment of FIG. 8, except electrical leads 96 and 98 traverses through feedthroughs 92 and 94 to make a case neutral design.

If the battery shares electrolyte (or a common electrode), the cells do not directly short if one of the cells has an internal short because in order to have such an internal short, two conditions are required. First, there must be a direct electrical connection between an anode and a cathode. Second, there must be an ionic pathway between the electrically connected anode and cathode in order to have a complete circuit. In our examples, the second condition is present, but not the first. For the historical method of connecting two entirely separate cells in series, we have the first condition, but not the second. Thus, it would be impossible to place two cells in series in the same enclosure (with a common electrolyte) because both conditions are met and the cells would short. In a parallel configuration, however, it is possible to enclose them with the same electrolyte because there is no electrical pathway between the anode and cathode.

It will be appreciated that the present invention can take many forms and embodiments. The true essence and spirit of this invention are defined in the appended claims, and it is not intended that the embodiment of the invention presented herein should limit the scope thereof.

What is claimed is:

1. An implantable medical device comprising:
    a hermetic enclosure;
    a low-power control circuit located in the enclosure;

a high-power output circuit located in the enclosure for delivering an electrical pulse therapy; and a power source and circuitry located in the enclosure for powering the low-power control circuit and the high-power output circuit, the power source and circuitry, said power source and circuitry further comprising:

a first high-rate cell having a resistance R;

a second high-rate cell having a resistance R;

wherein the first high-rate cell and second high-rate cell are electrically connected in parallel to the low-power control circuit and the high-power output circuit; and at least one resistive load having a resistance at least 10 times greater than the resistance R electrically connected between the first high-rate cell and the second high-rate cell, the at least one resistive load having a resistive value to limit, in the event the first high-rate cell being internally shorted, the rate at which such internally shorted first high-rate cell drains the second high-rate cell.

2. An implantable medical device of claim 1, wherein the at least one resistive load value being between 10 ohms and 100 ohms.

3. An implantable medical device of claim 1, wherein the first high-rate cell and the second high-rate cell include an electrode surface area up to 90 cm$^2$ each.

4. An implantable medical device of claim 3, wherein the electrode surface area being between 65 cm$^2$ and 90 cm$^2$.

5. An implantable medical device of claim 1, wherein the first high-rate cell and the second high-rate cell are maintained within a single case.

6. An implantable medical device of claim 1, wherein the first high-rate cell and the second high-rate cell includes a cathode, and further wherein the first high-rate cell and the second high-rate cell share a common anode.

7. An implantable medical device of claim 1, wherein the first high-rate cell and the second high-rate cell includes an anode, and further wherein the first high-rate cell and the second high-rate cell share a common cathode.

8. An implantable medical device of claim 7, wherein the cathode being selected from the group consisting of sliver oxide, vanadium oxide, silver vanadium oxide, manganese dioxide, copper oxide, copper silver vanadium oxide, lead oxide, carbon monoflouride, chromium oxide, bismuth-containing oxide, copper sulfate, and mixtures thereof.

9. An implantable medical device of claim 8, wherein the anode of the first high-rate cell and the anode of the second high-rate cell are formed from lithium.

10. An implantable medical device of claim 1, further comprising a switching circuit electrically connected between the first high-rate cell and the second high-rate cell for selectively coupling the first high-rate cell to the second high-rate cell upon activation of the high-power output circuit.

11. An implantable medical device having a hermetic enclosure for an, electrochemical battery, comprising:
a) a first high-rate electrochemical cell having a resistance R comprising:
   i) a first anode;
   ii) a first terminal for connecting the first anode to a first external lead;
   iii) a first electrolyte operatively associated with the first anode; and
b) a second high-rate electrochemical cell having a resistance R comprising:
   i) a second anode;
   ii) a second terminal for connecting the second anode to a second external lead;
   iii) a second electrolyte operatively associated with the second anode; and
c) a cathode electrically associated with the first electrolyte and the second electrolyte, wherein the first cell being connected in parallel to the second cell; and
d) at least one resistive load having a resistance at least 10 times greater than the resistance R electrically connected between the first external lead and the second external lead.

12. An electrochemical battery of claim 11 wherein the first and second high-rate cells discharge at a generally equal rate.

13. An electrochemical battery of claim 11 wherein the first high-rate cell and the second high-rate cell are housed in one casing.

14. An electrochemical battery of claim 11 wherein the first electrolyte and the second electrolyte are the same electrolyte.

15. An electrochemical battery of claim 11 wherein the at least one resistive load has a resistive value to reduce, in the event of an internal short in one of the high-rate cells, the rate at which the shorted high-rate cell drains the other high-rate cell.

16. An electrochemical battery of claim 15 wherein either high rate cell being able to provide power for a circuit in the event of a short in the other high rate cell.

17. An electrochemical battery of claim 15, wherein the at least one resistive load value being between 10 ohms and 100 ohms.

18. An electrochemical battery of claim 11, wherein the first high-rate cell and the second high-rate cell has a combined anode and cathode surface area of up to 180 cm$^2$.

19. An electrochemical battery of claim 18, wherein the combined anode and cathode surface area being between 130 cm$^2$ and 180 cm$^2$.

20. An electrochemical battery of claim 11, wherein the first terminal and the second terminal are the same.

21. A method for manufacturing an implantable medical device having a hermetic enclosure for an, electrochemical battery comprising the steps of:
a) providing a first high-rate electrochemical cell having a resistance R, comprising the steps of:
   i) providing a first cathode;
   ii) connecting a first external lead to the first cathode;
   iii) activating the first high-rate cell with an electrolyte solution operatively associated with the first cathode; and
b) providing a second high-rate electrochemical cell having a resistance R, comprising the step of:
   i) providing a second cathode;
   ii) connecting a second external lead to the second cathode;
   ii) activating the second electrochemical cell with the electrolyte solution operatively associated with the second cathode; and
c) associating an anode electrically with the electrolyte in the first high-rate cell and the second high-rate cell, wherein the first cell being connected in parallel to the second cell; and
d) connecting at least one resistive load having a resistance at least 10 times greater than the resistance R electrically between the first external lead and the second external lead.

22. A method of claim 21 wherein the first and the second high-rate cells discharge at a generally equal rate.

23. A method of claim 21 further comprising the steps of connecting electrically the anode to a battery casing to provide a negative charge on the casing.

24. A method of claim 21 wherein the cathode of the first high-rate cell and the cathode of the second high-rate cell are selected from the group consisting of sliver oxide, vanadium oxide, silver vanadium oxide, manganese dioxide, copper oxide, copper silver vanadium oxide, lead oxide, carbon monoflouride, chromium oxide, bismuth-containing oxide, copper sulfate, and mixtures thereof.

25. A method of claim 21, wherein the anode being formed from lithium.

26. A method for manufacturing an implantable medical device comprising the steps of:
   a) providing a hermetic enclosure;
   b) providing a low-power control circuit in the enclosure;
   c) providing a high-power output circuit in the enclosure for delivering an electrical pulse therapy; and
   d) providing a power source and circuitry in the enclosure for powering the low-power control circuit and the high-power output circuit, comprising the steps of:
      i) providing a first high-rate cell having a resistance R;
      ii) providing a second high-rate cell having a resistance R;
      iii) connecting the first cell and second cell electrically in parallel to the low-power control circuit and the high-power output circuit; and
      iv) connecting at least one resistive load having a resistance at least 10 times greater than the resistance R electrically between the first high-rate cell and the second high-rate cell.

27. A method of claim 26, wherein the at least one resistive load has a resistive value to limit, in the event of an internal short in one of the high-rate cells, the rate at which the shorted high-rate cell drains the other high-rate cell.

28. A method of claim 26, wherein the at least one resistive load value being between 10 ohms and 100 ohms.

29. A method of claim 26, wherein the first high-rate cell and the second high-rate cell has an electrode surface area up to 90 cm$^2$ each.

30. A method of claim 29, wherein the electrode surface area being between 65 cm$^2$ and 90 cm$^2$.

31. A method of claim 26, wherein the first high-rate cell and the second high-rate cell are maintained within a single case.

32. A method of claim 26, further comprising the step of connecting a switching circuit electrically between the first high-rate cell and the second high-rate cell for selectively coupling the first high-rate cell to the second high-rate cell upon activation of the high-power output circuit.

33. An implantable medical device comprising:
   a hermetic enclosure;
   a low-power control circuit located in the enclosure;
   a high-power output circuit located in the enclosure for delivering an electrical pulse therapy; and
   a power source and circuitry located in the enclosure for powering the low-power control circuit and the high-power output circuit, the power source and circuitry, said power source and circuitry further comprising:
   a first high-rate cell;
   a second high-rate cell;
   wherein the first high-rate cell and second high-rate cell are electrically connected in parallel to the low-power control circuit and the high-power output circuit, the first high-rate cell and the second high-rate cell includes an anode, and further wherein the first high-rate cell and the second high-rate cell share a common cathode; and
   at least one resistor electrically connected between the first high-rate cell and the second high-rate cell, the at least one resistive load having a resistive value to limit, in the event the first high-rate cell being internally shorted, the rate at which such internally shorted first high-rate cell drains the second high-rate cell, wherein the at least one resistive load value being between 10 ohms and 100 ohms,
   wherein the first high-rate cell and the second high-rate cell include an electrode surface being between 65 cm$^2$ and 90 cm$^2$.

* * * * *